(12) United States Patent
Pardal Filipe et al.

(10) Patent No.: US 10,226,460 B2
(45) Date of Patent: *Mar. 12, 2019

(54) PHARMACEUTICALLY ACCEPTABLE SALTS OF PIRLINDOLE ENANTIOMERS FOR USE IN MEDICINE

(71) Applicant: TECNIMEDE SOCIEDADE TECNICO-MEDICINAL S.A., Sintra (PT)

(72) Inventors: Augusto Eugenio Pardal Filipe, Lisbon (PT); Pedro Filipe Eufrasio Pedroso, Lisbon (PT); Susana Marques Almeida Pecorelli, Alcabideche (PT); Carlos Alberto Eufrasio Casimiro Caixado, Mafra (PT); Ana Sofia da Conceicao Lopes, Milharado (PT); Joao Carlos Ramos Damil, Torres Vedras (PT); Pedro Paulo de Lacerda E Oliveira Santos, Queluz (PT)

(73) Assignee: TECNIMEDE SOCIEDADE TECNICO-MEDICINAL S.A., Sintra (PT)

( * ) Notice: Subject to any disclaimer, the term of this patent is extended or adjusted under 35 U.S.C. 154(b) by 0 days.

This patent is subject to a terminal disclaimer.

(21) Appl. No.: 15/309,981

(22) PCT Filed: May 9, 2014

(86) PCT No.: PCT/PT2014/000026
§ 371 (c)(1),
(2) Date: Nov. 9, 2016

(87) PCT Pub. No.: WO2015/171002
PCT Pub. Date: Nov. 12, 2015

(65) Prior Publication Data
US 2017/0143710 A1 May 25, 2017

(51) Int. Cl.
*A61K 31/4985* (2006.01)

(52) U.S. Cl.
CPC ................ *A61K 31/4985* (2013.01)

(58) Field of Classification Search
CPC .................................................. A61K 31/4985
USPC .......................................................... 514/250
See application file for complete search history.

(56) References Cited

U.S. PATENT DOCUMENTS

| 5,053,407 | A | 10/1991 | Hayakawa et al. | |
|---|---|---|---|---|
| 9,682,986 | B2 * | 6/2017 | Pardal Filipe | ....... C07D 487/06 |
| 9,814,712 | B2 * | 11/2017 | Pardal Filipe | ..... A61K 31/4985 |
| 2004/0106681 | A1 * | 6/2004 | Rao | ........ A61K 31/00 514/620 |
| 2017/0145015 | A1 * | 5/2017 | Pardal Filipe | ....... A61K 9/2095 |

FOREIGN PATENT DOCUMENTS

WO 2006048242 A2 5/2006

OTHER PUBLICATIONS

Berge et al., Pharmaceutical Salts, Jan. 1977, Journal of Pharmaceutical Sciences, vol. 66, No. 1, pp. 1-9 (Year: 1977).*
Tullio et al., First Preparative Enantiomer Resolution of Pirlindole, a Potent Antidepressant Drug, 1998, Helvetica Chimica Acta, vol. 81, 539-547 (Year: 1998).*
Pascal de Tullio et al.; "Effective resolution of racemic pirlindole at the preparative scale"; Chirality, vol. 11, No. 4, Mar. 29, 1999 (Mar. 29, 1999), pp. 261-266, XP055131009.
A J Repta et all.; "Utilization of an enantiomer as a solution to a pharmaceutical problem: Application to solubilization of 1,2-di(4-piperazine-2,6-dione)propane"; Journal of Pharmaceutical Sciences, vol. 65, No. 2, Feb. 1976 (Feb. 1976), pp. 238-242, XP055130861.
C.-H. Gu, D. J. W. Grant; "Physical Properties and Crystal Structures of Chiral Drugs"; "5" In: Michel F. Eichelbaum, Bernard Testa, Andrew Somogyi (Editors): "Stereochemical Aspects of Drug Action and Disposition (Handbook of Experimental Pharmacology)", Apr. 10, 2003 (Apr. 10, 2003), Springer, XP009179283.
International Search Report dated Jul. 31, 2014 and Written Opinion of the International Searching Authority for PCT/PT2014/000026.

* cited by examiner

*Primary Examiner* — Kristin A Vajda
(74) *Attorney, Agent, or Firm* — Sughrue Mion, PLLC

(57) ABSTRACT

The present invention provides pharmaceutically acceptable salts of enantiomerically pure (R)-pirlindole and (S)-pirlindole compounds having an increased bioavailability profile for use in medicine.

6 Claims, No Drawings

PHARMACEUTICALLY ACCEPTABLE SALTS OF PIRLINDOLE ENANTIOMERS FOR USE IN MEDICINE

The present invention relates to novel pharmaceutically acceptable salts of enantiomerically pure (R)-pirlindole and (S)-pirlindole compounds useful in medicine.

BACKGROUND

Active pharmaceutical ingredients are frequently delivered to the patient in, for example, a solid-state as part of an approved dosage form. These active ingredients can exist in a variety of distinct solid forms, having each of them unique physiochemical properties that influence the bioavailability, e.g. dissolution and absorption of the drug. All of these technical characteristics are critical for development of the final drug product.

In particular, for a pharmaceutical molecule to be "active" it has to reach it site of action in the body. Most often the molecules are not directly "bioavailable", and are thus not directly absorbed in the body. In order to be absorbed, the molecules have to show adequate solubility and dissolution rates.

Dissolution of the molecule usually takes place in the stomach (for oral dosage forms), whereas the absorption takes place in the intestines. In the stomach the pH is quite low (varying from 1 to 5 depending on the individual), i.e. the initial dissolution takes place in a quite acidic environment. As many pharmaceutical products are either acids or bases it implies that the solubility/dissolution thereof is very dependant on the pH, so when evaluating the bioavailability of drugs pH dissolution values plays a crucial role.

Pirlindole, 2,3,3a,4,5,6-hexahydro-1H-8-methyl-pyrazine [3,2,1-j,k]carbazole, is a tetracyclic compound well known in medicine as being a reversible monoamine oxidase A inhibitor, useful as a medicament in the treatment of depression.

Further, pirlindole has also been shown to be useful for the treatment of diseases characterized by hyperproliferation of keratinocytes and/or T cells, in particular psoriasis and neurodermatisitis, as described in United States Patent Application US 2008/0254106.

Pirlindole pharmaceutically active forms include the mesylate and hydrochloride salts thereof.

However, therapeutic treatment methods with pirlindole have shown that there still exists field of improvement as regards the provision of alternative forms of the parent compound pirlindole which show an improved dissolution rate and solubility rate adequate for drug developing purposes.

The present invention therefore provides new, alternative and stable forms of pirlindole showing unexpectedly superior dissolution rates in acid environment, which result in increased absorption rates of the said active ingredient and thus are specially suitable to be used in medicine.

BRIEF DESCRIPTION OF THE INVENTION

The inventors of the present invention have found that specific salts of both enantiomers, (S)-pirlindole and (R)-pirlindole show unexpected superior solubility rates in an acidic environment, thus providing for unexpected superior dissolution profiles of the active ingredient in the stomach and as a consequence thereof superior adsorption in the intestines.

It is therefore an object of the present invention the provision of pharmaceutically acceptable salts of pirlindole enantiomers for use in medicine.

Therefore, a first object of the invention are pharmaceutically acceptable salts of pirlindole enantiomers for use in medicine characterized in that the pirlindole enantiomers are enantiomerically pure (R)-pirlindole or (S)-pirlindole.

A still further object of the present invention are pharmaceutically acceptable salts of pirlindole enantiomers for use in medicine characterized in that the pharmaceutically acceptable salts of (R)-pirlindole or (S)-pirlindole are salts of organic, inorganic or optically active acids.

An additional object of the present application are pharmaceutically acceptable salts of pirlindole enantiomers for use in medicine characterized in that these salts are salts of organic and inorganic acids of (R)-pirlindole or (S)-pirlindole, wherein the organic and inorganic acids are selected from the group consisting of: hydrochloric acid, hydrobromic acid (HBR), sulfuric acid, phosphoric acid, citric acid, anhydrous citric acid, mandelic acid, succinic acid and methanesulfonic acid.

A further object of the present invention are pharmaceutically acceptable salts of pirlindole enantiomers for use in medicine characterized in that the optically active acids forming the pharmaceutically acceptable salts of (R)-pirlindole or (S)-pirlindole are selected from the group consisting of: (S)-mandelic acid, (R)-mandelic acid, (R)-(+)-α-methoxy-α-trifluoromethylphenylacetic acid, (S)-(−)-α-methoxy-α-trifluoromethylphenylacetic acid, (1S,3R)-(−)-camphoric acid, (1R,3S)-(+)-camphoric acid, L-(−)-malic acid, D-(+)-malic acid, or similarly well known in the art optically active acids.

An additional object of the present invention are pharmaceutically acceptable salts of pirlindole enantiomers for use in medicine characterized in that the salts are selected from the group consisting of: (S)-pirlindole (R)-mandelate, (R)-pirlindole (S)-mandelate, (R)-pirlindole hydrobromide, (S)-pirlindole hydrobromide, (S)-pirlindole citrate, (R)-pirlindole citrate, (S)-pirlindole mesylate and (R)-pirlindole mesylate.

A still further object of the present invention are pharmaceutical compositions for use in medicine comprising pharmaceutically acceptable salts of pirlindole enantiomers as previously defined with pharmaceutically acceptable carriers, vehicles or excipients.

A final object of the present invention are pharmaceutical compositions suitable for oral administration in the form of tablets, granules, fine granules, capsules, powders and pills.

DESCRIPTION OF THE INVENTION

Pirlindole has an asymmetric carbon atom, which implies that the molecule can exist in the form of two enantiomers, (S)-pirlindole and (R)-pirlindole.

To date, however, there is no pharmaceutical product for any of those enantiomers, either already approved or awaiting approval, and only the use of the racemate form, as a salt of hydrochloric acid, is known in medicine.

The inventors of the present invention have found that specific salts of both enantiomers, (S)-pirlindole and (R)-pirlindole show unexpected superior solubility rates in an acidic environment, thus providing for unexpected superior dissolution profiles of the active ingredient in the stomach, superior adsorption in the intestines and as a consequence thereof an unexpectedly superior bioavailability profile of the active ingredient.

These salts of (S)-pirlindole and (R)-pirlindole are new compounds, not disclosed before in the prior art, as according to the available prior art, no suitable method existed for providing the pharmaceutically acceptable salts of these optically active compounds.

To this regard, the publication *Chirality* 11:261-266 (1999), fails to obtain pharmaceutically acceptable salts of the enantiomers of pirlindole by selective crystallization with optically active acids on an industrial scale. The document describes the use of the derivatization technique in conjunction with preparative chromatography.

However, for the purpose of the present invention, the inventors of the present application were able to obtain enantiomerically pure (R)-pirlindole and (S)-pirlindole by crystallization with optically active acids, in the form of pharmaceutically acceptable salts.

The obtention of the pharmaceutically acceptable salts of the enantiomers of pirlindole, led the present inventors to the findings on which the present application is based.

The salt of the pirlindole racemic mixture, (rac)-pirlindole hydrochloride, is to date the only salt form which is currently used in pharmaceutical dosage forms. To this regard it is well known that the said active pharmaceutical ingredient presents some difficulties concerning solubility, especially when administered in a subject who presents a highly acidic stomach pH of about 1-2, and as a consequence thereof, therapeutic treatments with such active ingredient are connected to poor absorption of the active ingredient and thus low bioavailability of the therapeutic agent.

To this regard, bioavailability describes the fraction of an administered dose of unchanged drug substance that reaches systemic circulation after a particular route of administration. Bioavailability is affected by first pass metabolism, solubility and instability of the drug substance. When a drug substance is administered by intravenous route its bioavailability is 100%. However, when drug substance is administered via other routes (such as orally), its bioavailability decreases due to incomplete absorption and first pass metabolism. The low bioavailability is linked with a poor presence of the drug substance at the place of action (e.g., receptor, enzyme, ion channel) and therefore the pharmacological activity is compromised.

The inventors of the present invention have also found that the solubility of (rac)-pirlindole hydrochloride in 0.1 N HCl is around 1.6 g/L which categorizes the product in that solvent media as slightly soluble and thus, with low bioavailability.

For the purpose of the present invention, the term "pharmaceutically acceptable salt" refers to those salts of (R)-pirlindole and (S)-pirlindole which are, within the scope of sound medical evaluation, suitable for use in contact with the tissues and organs of humans and lower animals without displaying toxicity, irritation, allergic response and the like and are commensurate with a reasonable benefit/risk ratio. Further, the pirlindole molecule has a secondary amine group, which has basic character and thus can form acid addition salts, which may be pharmaceutically acceptable acids.

Therefore, pharmaceutically acceptable salts according to the present invention include those pharmaceutically acceptable acid addition salts formed with organic and inorganic acids and those pharmaceutically acceptable salts formed with optically active acids.

Representative acid addition salts of (R)-pilindole and (S)-pirlindole include, but are not limited to, acetate, adipate, alginate, citrate, aspartate, benzoate, benzenesulfonate, bisulfate, butyrate, camphorate, camphorsulfonate, digluconate, fumarate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Non-limiting examples of acids that can be used to form pharmaceutically acceptable acid addition salts with (R)-pilindole and (S)-pirlindole include inorganic acids such as hydrochloric acid, hydrobromic acid (HBR), sulfuric acid and phosphoric acid and organic acids such as citric acid, anhydrous citric acid, mandelic acid, succinic acid and methanesulfonic acid.

Non-limiting examples of "optically active acids" that can be used to form pharmaceutically acceptable acid addition salts with (R)-pirlindole and (S)-pirlindole include (S)-mandelic acid, (R)-mandelic acid, (R)-(+)-α-methoxy-α-trifluoromethylphenylacetic acid. (S)-(−)-α-methoxy-α-trifluoromethylphenylacetic acid, (1S,3R)-(−)-camphoric acid, (1R,3S)-(+)-camphoric acid, L-(−)-malic acid, D-(+)-malic acid, or similarly well known in the art optically active acids.

Pharmaceutically acceptable salts of pirlindole enantiomers according to the present invention include:

(S)-pirlindole (R)-mandelate, (R)-pirlindole (S)-mandelate, (R)-pirlindole hydrobromide, (S)-pirlindole hydrobromide, (S)-pirlindole citrate, (R)-pirlindole citrate, (S)-pirlindole mesylate and (R)-pirlindole mesylate, (S)-pirlindole (R)-(+)-α-methoxy-α-trifluoromethylphenylacetic acid, (S)-pirlindole benzenesulfonate, (R)-pirlindole p-toluenesulfonate, (S)-pirlindole bisulfate, (R)-pirlindole oxalate, (R)-pirlindole maleate, (S)-pirlindole acetate, (S)-pirlindole glutamate, (S)-pirlindole lactate, (R)-pirlindole adipate, (R)-pirlindole benzoate and (S)-pirlindole malate.

As said before, surprisingly the inventors of the present invention have found that pharmaceutically acceptable salts of pirlindole enantiomers, ((R)-pirlindole and (S)-pirlindole) show unexpectedly superior solubility rates in a highly acidic pH, and are thus especially suitable for use in medicine.

The following assay shows the unexpected superior solubility rates of pharmaceutically acceptable salts of (R)-pirlindole and (S)-pirlindole according to the present invention versus the (rac)-pirlindole hydrochloride salt, known from the state of the art.

The Solubility test performed for showing the present invention's advantages is well known in the state of the art and is based on the "Classical saturation shake-flask method", which comprises: Agitation at 37° C. during 15 h of supersaturated solution of the solid in HCl (aq) 0.1N, followed by filtration, dilution with water and quantification by UV measurement at 267 nm wavelength.

The results obtained are shown in the following Table 1.

TABLE 1

| Data solubility in 0.1N HCl | |
|---|---|
| Compound | * Solubility (g/L) |
| R-pirlindole-S-mandelate | 5.8 |
| S-pirlindole-R-mandelate | 5.4 |
| R-pirlindole hydrobromide | 4.8 |
| R-pirlindole citrate | 5.9 |
| R-pirlindole mesylate | 6.4 |
| S-pirlindole hydrobromide | 4.7 |
| S-pirlindole mesylate | 7.0 |

TABLE 1-continued

Data solubility in 0.1N HCl

| Compound | * Solubility (g/L) |
|---|---|
| S-pirlindole citrate | 6.8 |
| (rac)-pirlindole•HCl | 1.6 |

From the data presented in the Table 1, one can easily conclude that the solubility of the new salts of the enantiomers of pirlindole is 3 to 4 times higher than that of (rac)-pirlindole hydrochloride, which is a very significant and surprising result.

The method used for obtaining the pharmaceutically acceptable salts of (R)-pirlindole and (S)-pirlindole contemplated in the present invention comprises crystallization of (rac)-pirlindole in the free base form with optically active acids in an organic solvent and, optionally its subsequent salification to form pharmaceutically acceptable salts with pharmaceutically acceptable acids.

The method comprises the following steps:

i) Dissolving (rac)-pirlindole hydrochloride in aqueous solvent, followed by a subsequent extraction with a chlorinated solvent and complete removal of the solvent to obtain (rac)-pirlindole in the free base form;

ii) Dissolving the (rac)-pirlindole obtained in step i) in an organic solvent, followed by adding an optically active acid for resolution;

iii) Stirring for 15 min to 2 h the suspension formed in ii) while diastereomeric salt precipitation occurs;

iv) Filtering the obtained diastereomeric salt and purifying it by suspension in an organic solvent to obtain (S)-pirlindole or (R)-pirlindole enantiomer in the form of a pharmaceutically acceptable salt formed with the optically active acid;

In addition to the detailed process steps, and where the products to be obtained are (S)-pirlindole or (R)-pirlindole enantiomer as a pharmaceutically acceptable acid addition salt with suitable organic and inorganic acids, the said process contemplates optionally the following steps v) Obtaining enantiomerically pure (S)-pirlindole and/or (R)-pirlindole as a free base by dissolution of the product obtained in step iv) in an aqueous solvent, subsequent extraction with chlorinated solvent and complete removal of the solvent; and vi) Obtaining S)-pirlindole or (R)-pirlindole in the form of pharmaceutically acceptable acid addition salts by salification of the enantiomerically pure (S)-pirlindole and/or (R)-pirlindole in the form of a free base obtained in step v) with a pharmaceutically acceptable acid to form a pharmaceutically acceptable acid addition salt of S)-pirlindole or (R)-pirlindole enantiomer.

For the purposes of the present invention the term "aqueous solvent" refers, for example, to deionized water.

For purposes of this invention the term "organic solvent" refers to solvents commonly used in organic chemistry or mixtures thereof in any proportions.

Non-limiting examples of organic solvents used in steps ii) and iv) of the process of the present invention are selected from the group consisting of: methanol, ethanol, propanol, 1-butanol, 2-butanol, tert-butyl alcohol, 2-butanone, acetone, ethyl methyl ketone, methyl isobutyl ketone, dimethyl sulfoxide, 1,2-dichloroethane, diethyl ether, dimethyl ether, dimethylformamide, methyl tert-butyl ether, 2-propanol, pyridine, toluene, xylene and the like, and mixtures thereof in any proportion.

Preferred are the following solvents: ethanol, methanol, 1-butanol, 2-butanol, tert-butyl alcohol, acetone, methyl ethyl ketone and isopropanol as well as mixtures thereof in any proportions, such as isopropanol/acetone (1:1), ethanol/acetone (1:1), ethanol/methyl isobutyl ketone (1:1) and ethanol/1-butanol (1:4).

For purposes of this invention the term "chlorinated solvent" means chloroform, dichloromethane, methylene chloride, trichloromethane or carbon tetrachloride, or mixtures thereof in any proportions.

For purposes of this invention, it is considered as enantiomerically pure when enantiomeric purity as calculated by chiral chromatography or specific optical rotation is equal to or greater than 97%.

The present invention further provides new pharmaceutical dosage forms comprising new pharmaceutically acceptable salts of (R)-pirlindole and new pharmaceutically acceptable salts of (S)-pirlindole according to the present invention together with pharmaceutically acceptable carriers, vehicles and/or suitable excipients.

The term "pharmaceutically acceptable carrier, vehicle or excipient" as used here, means a solid, semi-solid or inert fluid excipient, filler, encapsulating or formulation aiding material of any kind already known by one skilled in the art.

Pharmaceutical compositions of the present invention can be formulated to be administered to humans and other mammals orally, (in liquid or solid forms) rectally, parenterally, intracisternally, intravaginally, intraperitoneally, topically (in the form of powders, ointments or drops), buccally or in the form of an oral or nasal spray. The term "parenterally", as used here, refers to modes of administration, including intravenous, intramuscular, intraperitoneal, intrasternal, subcutaneous, intra-articular injection and infusion.

Pharmaceutical compositions for parenteral injection include aqueous or non-aqueous solutions, dispersions, suspensions or emulsions, pharmaceutically acceptable sterile or non-sterile, and powders for reconstitution in sterile injectable solutions or dispersions.

If it is required, and for a more effective distribution, the compounds of the invention can be embedded in extended controlled release or directed administration systems, such as polymeric matrices, liposomes and microspheres.

The pharmaceutical composition of the present invention is preferably a solid composition for oral administration, and specific examples thereof include tablets, granules, fine granules, capsules, powders, and pills.

The solid oral composition of the present invention can have an excipient, a binder, a lubricant and the like added thereto, in addition to the pharmaceutically acceptable salt of (R)-pirlindole or (S)-pirlindole, and can be formulated into the respective forms. Examples of excipients that may be used include lactose, corn starch, crystalline cellulose, sucrose, glucose, mannitol, sorbitol, and calcium carbonate. Examples of the binder include hydroxypropyl cellulose, hydroxyethyl cellulose, hypromellose, hydroxyethylethyl cellulose, hydroxyethylmethyl cellulose, polyvinylpyrrolidone, and polyvinyl alcohol. Examples of the lubricant include magnesium stearate, stearic acid, palmitic acid, calcium stearate, and talc.

Such formulations are described in detail in a number of sources which are well known and readily available to those skilled in the art. For example, Remington's The Science and Practice of Pharmacy, edited by Allen, Loyd V., Jr, 22nd edition, describe the making of formulations which can be used in connection with the subject invention.

Further, there are no particular limitations on the method for preparing the solid pharmaceutical compositions of the present invention, but for example, in the case of tablets, the tablets may be produced by uniformly mixing the various components described above, and producing the tablets by a general-purpose wet granulation compression method, a direct powder compression method, or the like. Furthermore, the tablets thus obtained may be further subjected to film coating, sugar coating, sustained release coating, or the like, such as, embedded in extended controlled release or directed administration systems, such as polymeric matrices, liposomes and microspheres. In this case, examples of the possible coating agent include hypromellose, hydroxypropyl cellulose, polyvinyl alcohol, titanium oxide, talc, polyethylene glycol, triethyl citrate, stearic acid, hydrated silicon dioxide, and light silicic anhydride. Examples of the sugar coating include gum arabic, purified gelatin, gelatin, purified sucrose, sucrose, precipitated calcium carbonate, talc, and calcium dihydrogen phosphate hydrate. Examples of the sustained release coating agent include methacrylic acid copolymer LD, ethyl cellulose, aminoalkyl methacrylate copolymer RS, and hypromellose.

The dosage of the active ingredients of the present invention administered to an individual will be dependent upon the response desired and may be dependent upon the subject to be treated, its age, health, weight, frequency of treatment etc. For example, dosage levels contemplated according to the present invention comprise, from 0.1 to 10 mg/kg for oral administration, from 0.01 to 10 mg/kg for intravenous administration.

EXAMPLES

The examples below are intended to illustrate the invention and should not be construed as limiting thereof.

Example 1

(R)-pirlindole (S)-mandelate 100 g (0.38 mole) of (R,S)-pirlindole hydrochloride are dissolved in 16 L deionized water at room temperature. To the solution are added 42.4 g (0.4 mole) of anhydrous sodium carbonate and stir for 1-2 h.

The above solution is extracted with 3×4 L of dichloromethane and the combined organic phases are dried over sodium sulfate and evaporated under vacuum to dryness.

To the concentrate was added 2 L of acetone.

To the above solution is added, under stirring, a solution of 27.6 g (0.18 mole) of (S)-mandelic acid in 150 ml of acetone.

The precipitated product is filtered, washed with 2×100 mL of acetone and dried under vacuum at 35° C.-45° C.

The above product is suspended in ethanol (250 mL) and is subsequently filtered and dried under vacuum at 35° C.-45° C., yielding 48.5 g (0.13 mole) of (R)-pirlindole (S)-mandelate, (yield=68%). Chiral HPLC (enantiomeric purity=98.2%).

Example 2

(S)-pirlindole (R)-mandelate

Using the same procedure as in Example 1, starting from 100 g (0.38 mole) of (R,S)-pirlindole hydrochloride and using 27.6 g (0.18 mole) of (R)-mandelic acid, yielded 45.6 g (0.12 mole) of (S)-pirlindole (R)-mandelate (yield=63%). Chiral HPLC (enantiomeric purity=98.7%).

Example 3

(S)-pirlindole (R)-mandelate

Using the same procedure as in Example 1, except that a mixture of isopropanol/acetone (1:1) is used as the organic solvent, starting from 10 g (0.038 mole) of (R,S)-pirlindole hydrochloride and using 2.8 g (0.018 mole) of (R)-mandelic acid, yielded 4.1 g (0.011 mole) of (S)-pirlindole (R)-mandelate (yield=57.9%). Chiral HPLC (enantiomeric purity=98.1%).

Example 4

(S)-pirlindole (R)-(+)-α-methoxy-α-trifluoromethyl-phenylacetic Acid

Using the same procedure as in Example 1, except that a mixture of ethanol/acetone (1:1) was used as the organic solvent and as optically active acid, (R)-(+)-α-methoxy-α-trifluoromethylphenylacetic acid (8.3 g) (0.018 mole) was used, starting from 10 g (0.038 mole) of (R,S)-pirlindole hydrochloride, yielded 4.8 g (0.010 mole) of (S)-pirlindole (R)-(+)-α-methoxy-α-trifluoromethylphenylacetic acid (yield=52.6%). Chiral HPLC (enantiomeric purity=97.7%).

Example 5

(R)-Pirlindole hydrobromide

The product obtained in Example 1 (10 g, 0.027 mole) was dissolved in 550 ml of deionized water. The aqueous phase was extracted with 3×300 ml of chloroform. The combined organic phases were dried over sodium sulfate, evaporated to dryness under vacuum and 200 ml of acetone were added.

To the above solution, under stirring, a solution of 6 ml of HBr (48% aqueous solution) (0.04 mole) was added.

The dried precipitated product is filtered, washed with 2×10 ml of acetone and dried under vacuum at 35° C.-45° C.

The above product was suspended in ethanol/methyl isobutyl ketone (1:1) (250 mL) and was subsequently filtered and dried under vacuum at 35° C.-45° C., yielding 6.5 g (0.021 mole) of (R)-pirlindole hydrobromide (yield=77.8%). Chiral HPLC (enantiomeric purity=97.9%).

Example 6

(R)-Pirlindole citrate

The product obtained in Example 1 (10 g, 0.027 mole) was dissolved in 550 ml of deionized water. The aqueous phase was extracted with 3×300 ml of trichloroethane. The combined organic phases were dried over sodium sulfate, evaporated to dryness under vacuum and 200 ml of acetone were added.

To the above solution, under stirring 7.7 g of anhydrous citric acid (0.04 mole) were added.

The dried precipitated product was filtered, washed with 2×10 ml of acetone and dried under vacuum at 35° C.-45° C.

The above product was suspended in ethanol/1-butanol (1:4) (250 mL) and was subsequently filtered and dried under vacuum at 35° C.-45° C., yielding 9.2 g (0.020 mole) of (R)-pirlindole citrate (yield=74.1%). Chiral HPLC (enantiomeric purity=97.6%).

Example 7

(R)-Pirlindole mesylate

Starting from 10 g of (R)-pirlindole (S)-mandelate obtained in Example 1 and following the procedure described in Example 5 using methanesulfonic acid as pharmaceutical acceptable acid, 7.4 g (0.023 mole) of (R)-pirlindole mesylate were obtained (yield=85.2%). Chiral HPLC (enantiomeric purity=98.0%).

Example 8

(S)-pirlindole hydrobromide

Starting from 10 g of (S)-pirlindole (R)-mandelate obtained in Example 2 using hydrobromic acid as pharmaceutical acceptable acid, and following the procedure described in Example 6, 7.4 g (0.024 mole) of (S)-pirlindole hydrobromide were obtained (yield=88.9%). Chiral HPLC (enantiomeric purity=98.2%).

Example 9

(S)-pirlindole mesylate

Starting from 10 g of (S)-pirlindole (R)-mandelate obtained in Example 2 and following the procedure described in Example 6 using methanesulfonic acid as pharmaceutical acceptable acid, 6.8 g (0.021 mole) of (S)-pirlindole mesylate were obtained (yield=77.8%). Chiral HPLC (enantiomeric purity=98.0%).

Example 10

(S)-Pirlindole citrate

Starting from 10 g of (R)-mandelate of (S)-pirlindole obtained in Example 2 and following the procedure described in Example 6 using citric acid as pharmaceutical acceptable acid, 9.5 g (0.021 mole) of (R)-pirlindole citrate were obtained (yield=77.8%). Chiral HPLC (enantiomeric purity=98.5%).

Example 11

Pharmaceutical Compositions
Sachets of (S)-Pirlindole Mesylate (Amounts are Given in % Weight with Respect to the Total Composition)
(S)-Pirlindole mesylate . . . 1 to 99%
Lactose monohydrate . . . 99 to 1%

The manufacture of the sachets includes mixing all components, passing them through a sieve and, filling and packaging the mixture into a sachet.
Sachets of (R)-Pirlindole Mesylate (Amounts are Given in % Weight with Respect to the Total Composition)
(R)-Pirlindole mesylate . . . 1.5 to 98.5%
Lactose monohydrate . . . 98.5 to 1.5%

The manufacture of the sachets includes mixing all components, passing them through a sieve and, filling and packaging the mixture into a sachet.
Sachets of (S)-Pirlindole (R)-Mandelate (Amounts are Given in % Weight with Respect to the Total Composition)
(S)-Pirlindole (R)-mandelate . . . 1 to 99%
Lactose monohydrate . . . 99 to 1%

The manufacture of the sachets includes mixing all components, passing them through a sieve and, filling and packaging the mixture into a sachet.
Sachets of (R)-Pirlindole (S)-Mandelate (Amounts are Given in % Weight with Respect to the Total Composition)
(R)-Pirlindole (S)-mandelate . . . 2 to 98%
Lactose monohydrate . . . 98 to 2%

The manufacture of the sachets includes mixing all components, passing them through a sieve and, filling and packaging the mixture into a sachet.

Lisbon, May 8, 2014.

The invention claimed is:

1. A pharmaceutically acceptable salt of a pirlindole enantiomer for use in medicine, wherein the salt is selected from the group consisting of (R)-pirlindole-(S)-mandelate, (S)-pirlindole-(R)-mandelate, (R)-pirlindole hydrobromide, (R)-pirlindole-citrate, (R)-pirlindole mesylate, (S)-pirlindole hydrobromide, (S)-pirlindole mesylate and (S)-pirlindole citrate.

2. A pharmaceutical composition for use in medicine comprising the pharmaceutically acceptable salt according to claim 1 together with a pharmaceutically acceptable carrier, vehicle or excipient.

3. The pharmaceutical composition according to claim 2 which is in the form of a tablet, a granule, a fine granule, a capsule, a powder and a pill.

4. A pharmaceutically acceptable salt of a pirlindole enantiomer for use in medicine, wherein an acid forming the pharmaceutical acceptable salt is an optically active acid.

5. The pharmaceutically acceptable salt according to claim 4 wherein the pirlindole enantiomer is enantiomerically pure (R)-pirlindole or (S)-pirlindole.

6. The pharmaceutically acceptable salt according to claim 4, wherein the optically active acid forming the pharmaceutically acceptable salt of (R)-pirlindole or (S)-pirlindole is selected from the group consisting of (S)-mandelic acid, (R)-mandelic acid, (R)-(+)-α-methoxy-α-trifluoromethylphenylacetic acid, (S)-(−)-α-methoxy-α-trifluoromethylphenylacetic acid, (1S,3R)-(−)-camphoric acid, (1R,3S)-(+)-camphoric acid, L-(−)-malic acid and D-(+)-malic acid.

* * * * *